United States Patent
Sudo et al.

(10) Patent No.: US 9,675,256 B2
(45) Date of Patent: Jun. 13, 2017

(54) PHOTOACOUSTIC APPARATUS AND METHOD FOR CONTROLLING THE SAME

(71) Applicant: CANON KABUSHIKI KAISHA, Tokyo (JP)

(72) Inventors: Yoshiaki Sudo, Chigasaki (JP); Akira Sato, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/871,410

(22) Filed: Sep. 30, 2015

(65) Prior Publication Data

US 2016/0015274 A1    Jan. 21, 2016

Related U.S. Application Data

(63) Continuation of application No. 13/514,925, filed as application No. PCT/JP2010/007141 on Dec. 8, 2010, now Pat. No. 9,173,633.

(30) Foreign Application Priority Data

Dec. 11, 2009   (JP) ................... 2009-282288

(51) Int. Cl.
*A61B 8/08* (2006.01)
*A61B 5/00* (2006.01)

(52) U.S. Cl.
CPC .......... *A61B 5/0095* (2013.01); *A61B 5/0059* (2013.01); *A61B 8/08* (2013.01); *A61B 2560/0233* (2013.01); *A61B 2576/00* (2013.01)

(58) Field of Classification Search
CPC .......................... A61B 5/0095; A61B 2576/00

USPC ........................................................... 73/643
See application file for complete search history.

(56) References Cited

U.S. PATENT DOCUMENTS

| | | | | |
|---|---|---|---|---|
| 5,713,356 A | * | 2/1998 | Kruger | A61B 5/0091 600/407 |
| 5,840,023 A | * | 11/1998 | Oraevsky | A61B 5/0095 367/7 |
| 6,108,196 A | * | 8/2000 | Jung | E05B 17/0037 292/102 |
| 8,501,099 B2 | * | 8/2013 | Viator | G01N 21/1702 422/68.1 |

(Continued)

*Primary Examiner* — J M Saint Surin
(74) *Attorney, Agent, or Firm* — Canon USA, Inc. IP Division (57) ABSTRACT

Provided is a photoacoustic apparatus capable of recognizing variation in reception characteristic among a plurality of receiving elements that detect an acoustic wave in the photoacoustic apparatus, with a simple configuration unique to the photoacoustic apparatus.

A photoacoustic apparatus includes a detecting unit including a plurality of receiving elements configured to detect an acoustic wave that is generated when an analyte is irradiated with light; a signal processing unit configured to acquire information about the inside of the analyte from a detected signal acquired from the detecting unit; an optical absorber configured to absorb the irradiation light; and a reception characteristic calculation unit configured to calculate reception characteristic information of the plurality of receiving elements on the basis of detected signals when the plurality of receiving elements receive an acoustic wave that is generated from the optical absorber.

9 Claims, 5 Drawing Sheets

(56) References Cited

U.S. PATENT DOCUMENTS

| | | | |
|---|---|---|---|
| 9,173,633 B2 * | 11/2015 | Sudo .................... | A61B 5/0095 73/643 |
| 2002/0035327 A1 | 3/2002 | Kruger | |
| 2009/0198128 A1 * | 8/2009 | Fukutani .............. | A61B 5/0091 600/437 |

* cited by examiner

PHOTOACOUSTIC APPARATUS AND METHOD FOR CONTROLLING THE SAME

CROSS-REFERENCE TO RELATED APPLICATION

This application is a Continuation of U.S. application Ser. No. 13/514,925 filed Jun. 8, 2012, which is a National Phase application of International Application PCT/JP2010/007141, filed Dec. 8, 2010, which claims priority from Japanese Patent Application No. 2009-282288, filed Dec. 11, 2009, which are hereby incorporated by reference herein in their entireties.

TECHNICAL FIELD

The present invention relates to a photoacoustic apparatus that receives a photoacoustic wave generated when an analyte is irradiated with light.

BACKGROUND ART

A study on an optical imaging apparatus has been promoted in medical fields. The optical imaging apparatus irradiates a living body with light from a light source such as a laser, and forms an image of information about the inside of the living body obtained from the incident light. The optical imaging technique includes photoacoustic tomography (PAT). The photoacoustic tomography irradiates a living body with pulsed light generated from a light source and detects an acoustic wave generated from a living tissue absorbing the energy of the pulsed light propagating through and diffused in the living body (PTL 1). More specifically, the technique uses a difference in absorptance of light energy between a detected portion such as a tumor and the other tissues, and receives by receiving elements an elastic wave that is generated when part of the analyte absorbs the light energy and instantly expands. By analyzing the detected signal, an optical characteristic distribution, and more particularly, a light-energy absorption density distribution of the living body can be obtained. The information can be used in quantitative measurement for a specific substance in the analyte, for example, glucose or hemoglobin contained in the blood. Hence, the information can be used for specifying the position of a malignant tumor accompanying with the growth of new blood vessels.

The receiving elements of the probe are formed of piezoelectric elements. Variation in reception characteristic may appear among the receiving elements depending on their machining accuracies. Also, variation in reception characteristic may appear among ultrasonic receiving elements using the MEMS technique, which has been developed in recent years, even though the elements are fabricated by a semiconductor process. If the variation in reception characteristic appears among the receiving elements, in particular, if variation in sensitivity characteristic to a frequency band of the photoacoustic wave appears, variation in signal intensity of the photoacoustic wave received by the receiving elements appears among the receiving elements. The photoacoustic apparatus reconfigures an image based on the premise that the receiving elements have the equivalent sensitivities. Thus, if the variation in reception characteristic appears among the receiving elements, the variation in reception characteristic may result in intensity unevenness on a screen after the reconfiguration. The quantitative performance of the measurement may be degraded.

PTL 2 discloses a method for adjusting the sensitivity of an ultrasonic sensor. The ultrasonic sensor transmits an ultrasonic wave with a single frequency from an ultrasonic wave source, which is provided separately from the ultrasonic sensor, to the ultrasonic sensor, and adjusts output signals to decrease the difference (sensitivity difference) between the output signals that are converted by respective elements.

CITATION LIST

Patent Literature

[PTL 1]
U.S. Pat. No. 5,840,023
[PTL 2]
Japanese Patent Laid-Open No. 2004-125514

SUMMARY OF INVENTION

Technical Problem

When the variation in reception characteristic among the receiving elements, which receive the acoustic wave generated when the analyte is irradiated with the light, is adjusted, if the ultrasonic wave source is provided separately like PTL 2, the apparatus may increase in size.

If an ultrasonic echo (ultrasonic diagnostic apparatus) is used, since its probe has both transmitting and receiving functions of ultrasound, the sensitivity can be adjusted by the method like PTL 2 without a separately provided wave source. However, since photoacoustic waves typically have frequencies of about 1 MHz, the photoacoustic apparatus has to adjust the sensitivity within a frequency band corresponding to those frequencies. The ultrasonic diagnostic apparatus typically oscillates ultrasound with frequencies in a range from 8 to 10 MHz. It is difficult to oscillate the ultrasound with the frequencies of the photoacoustic waves.

The present invention is made in light of the situations. Hence, the present invention provides a photoacoustic apparatus capable of recognizing variation in reception characteristic among a plurality of receiving elements that detect an acoustic wave in the photoacoustic apparatus, with a simple configuration unique to the photoacoustic apparatus.

Solution to Problem

A photoacoustic apparatus according to an aspect of the present invention includes a detecting unit including a plurality of receiving elements configured to detect an acoustic wave that is generated when an analyte is irradiated with light; a signal processing unit configured to acquire information about the inside of the analyte from a detected signal acquired from the detecting unit; an optical absorber configured to absorb the irradiation light; and a reception characteristic calculation unit configured to calculate reception characteristic information of the plurality of receiving elements on the basis of detected signals when the plurality of receiving elements receive an acoustic wave that is generated from the optical absorber.

Advantageous Effects of Invention

With the aspect, since the photoacoustic apparatus includes the optical absorber, and the plurality of receiving elements receive the photoacoustic wave generated from the optical absorber, the variation in reception characteristic among the plurality of receiving elements can be recognized with the simple structure unique to the photoacoustic apparatus.

DESCRIPTION OF EMBODIMENTS

Embodiments of the present invention will be described in detail below with reference to the drawings. The same reference signs are applied to the same components, and the redundant description will be omitted.

[First Embodiment]
[Photoacoustic Apparatus]

Figure 1:
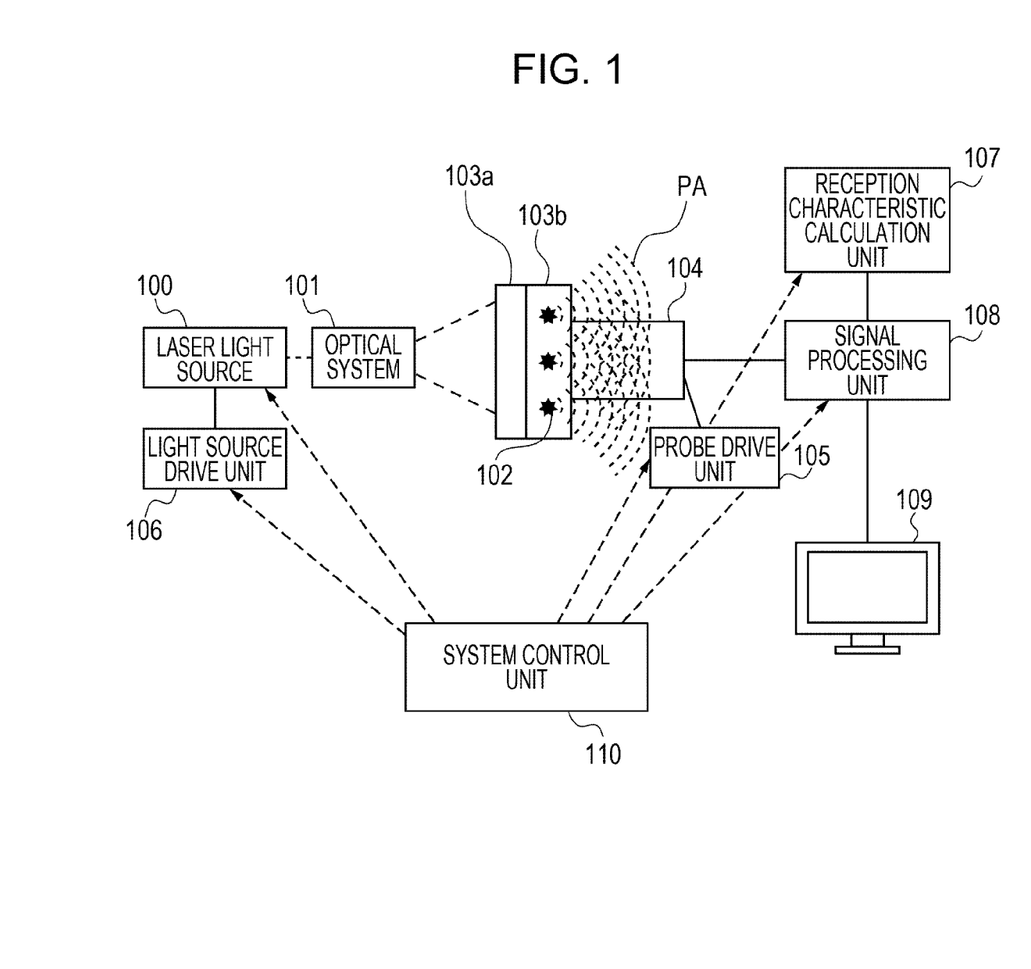
FIG. 1 is a block diagram schematically showing a configuration of a photoacoustic apparatus according to a first embodiment of the present invention.

A configuration of a photoacoustic apparatus according to a first embodiment will be described with reference to FIG. 1.

The photoacoustic apparatus according to this embodiment is a photoacoustic imaging apparatus that forms an image of information about the inside of an analyte. If the analyte is a living body, the photoacoustic apparatus can form an image of living body information for the purpose of diagnosis of a malignant tumor or a vascular disease, or follow-up of a chemical treatment. In the present invention, the "living body information" is an acoustic-wave source distribution generated through light irradiation. In particular, the "living body information" is an initial-sound-pressure distribution in the living body; a light-energy absorption-density distribution obtained by the former distribution; or a substance density distribution of substances that form a living tissue obtained by the former two distributions. For example, the substance density distribution may be oxygen saturation.

The photoacoustic apparatus according to this embodiment includes a laser light source 100 and a probe 104, as a basic hardware configuration. The laser light source 100 is a light source that irradiates the analyte with pulsed light. Now, measurement of the analyte will be described below.

The analyte (not shown), such as a living body, is fixed between plates 103a and 103b. The plates 103a and 103b face each other, and press and fix the analyte from both sides. The plates 103a and 103b are occasionally called pressure plates 103. The pulsed light from the light source is guided to a surface of the plate 103a by the optical system 101, that is, for example, a lens, a mirror, and/or an optical fiber. Hence, the pulsed light becomes diffused pulsed light and is emitted on the analyte. If part of light energy propagating through the analyte is absorbed by an optical absorber such as a blood vessel, an acoustic wave (typically, ultrasonic wave) is generated form the optical absorber due to thermal expansion. The acoustic wave is occasionally called "photoacoustic wave." That is, since the optical absorber absorbs the pulsed light, the optical absorber increases in temperature. The increase in temperature results in volumetric expansion of the optical absorber. Hence, an acoustic wave is generated. The pulsed light desirably has a certain time width that satisfies a confinement condition of heat and stress, to efficiently confine absorption energy in the optical absorber. The time width is typically in a range from about 1 to 200 nanoseconds.

The probe 104 that detects an acoustic wave corresponds to a detecting unit including a plurality of receiving elements that detect an acoustic wave. The detecting unit detects an acoustic wave generated in the analyte, and converts the acoustic wave into an electric signal (analog signal). The detected signal acquired by the detecting unit is also called "photoacoustic signal."

A signal processing unit 108 acquires information about the inside of the analyte from the photoacoustic signal. In the signal processing unit 108, a signal amplifier amplifies the photoacoustic signal acquired by the probe 104, and an A/D converter converts the signal into a photoacoustic signal as a digital signal. An image reconfiguration unit executes arithmetical processing for the digital signal to obtain three-dimensional information. Then, an image display unit 109 displays a photoacoustic image of the analyte. All elements are controlled by a system control unit 110.

[Light Source]

If the analyte is a living body, the light source emits light with a specific wavelength that is absorbed by a specific component included in the living body. The light source is desirably a pulsed light source that can emit pulsed light in a range from several nanoseconds to the order of several hundred nanoseconds. The light source is desirably a laser. Alternatively, a light-emitting diode may be used instead of the laser. The laser may be any of various lasers including a solid-state laser, a gas laser, a dye laser, and a semiconductor laser.

In this embodiment, the single light source is provided. However, a plurality of light sources may be used. If the plurality of light sources are used, to increase the light irradiation intensity for the living body, a plurality of light sources that oscillate light with the same wavelength may be used, or to measure a difference in optical characteristic distribution depending on wavelengths, a plurality of light sources that oscillate light with different wavelengths may be used. The light source may use a pigment that allows the wavelength of oscillated light to be changed, or the light source may be optical parametric oscillators (OPO). Accordingly, the difference in optical characteristic distribution depending on wavelengths can be measured. The use wavelength may be in a range from 700 to 1100 nm. Such wavelengths are absorbed by the living body only by a little amount. When the optical characteristic distribution of a living tissue located relatively near the surface of the living body is obtained, a wavelength range from 400 to 1600 nm, the range which is wider than the above wavelength range, may be used.

[Optical System]

The light emitted from the light source may propagate through an optical waveguide. Although not shown in FIG. 1, the optical waveguide may be an optical fiber. If the optical fiber is used, a plurality of optical fibers may be used for each of the light sources to guide the light to the surface of the living body. Alternatively, the light of the plurality of light sources may be guided to a single optical fiber, and the light may be guided to the living body through the single optical fiber. Still alternatively, a mirror that generally reflects light or an optical part, such as a lens that collects light, enlarges light, or changes the shape of light, may be used to guide the light. The optical part may be any part as long as a light irradiation region on the surface of the analyte is irradiated with the light emitted from the light source, in a manner with a desirable shape.

[Probe]

The probe (detecting unit) 104 detects an acoustic wave and converts the acoustic wave into an electric signal. The photoacoustic wave generated from the living body is an ultrasonic wave with frequencies in a range from 100 KHz to 100 MHz. Hence, the probe (analyte wave detecting unit) 104 is an ultrasonic wave detecting unit that can receive the frequencies in the aforementioned frequency band. The acoustic wave detecting unit may be, for example, a transducer using a piezoelectric phenomenon, a transducer using an optical resonance, or a transducer using a change in capacitance, as long as the unit can detect an acoustic wave signal. The probe 104 of this embodiment may include a plurality of receiving elements that are two-dimensionally arranged. Since the two-dimensionally arranged elements are used, the acoustic wave can be detected simultaneously at a plurality of positions. The detection time can be reduced, and the influence of vibration of the analyte can be reduced. Also, an agent for acoustic impedance matching, such as gel or water, may be used between the probe 104 and the analyte to suppress reflection of the sonic wave. Variation in reception characteristic among the plurality of receiving elements is the problem to be addressed by the present invention.

[Plate]

The plates 103a and 103b (pressure plates 103) each desirably have a light transparency that does not reduce the photoacoustic effect provided by the diffused pulsed laser, and an ultrasonic transparency that does not reduce the photoacoustic wave. Typically, the plates 103a and 103b may be made of acryl or polymethyl pentene. The plates 103a and 103b may have any thickness as long as the thickness provides an intensity that can suppress deformation of the plates 103a and 103b during holding. Typically, the plates 103a and 103b each have a thickness of about 10 mm.

[Optical Absorber]

The photoacoustic apparatus according to this embodiment includes an optical absorber 102 that particularly absorbs light that is emitted from the light source, as a feature of the photoacoustic apparatus. As the optical absorber 102 has a higher light absorptance, the photoacoustic wave is more efficiently generated. For example, the optical absorber 102 may be formed of a solid color substance such as graphite. If a specific analyte is present as a measurement subject, the optical absorber 102 may be made of a material that exhibits a photoacoustic characteristic obviously different from the photoacoustic characteristic of the analyte. To be more specific, if the analyte is a human body, for example, a black gel ball may be used.

Figure 2:
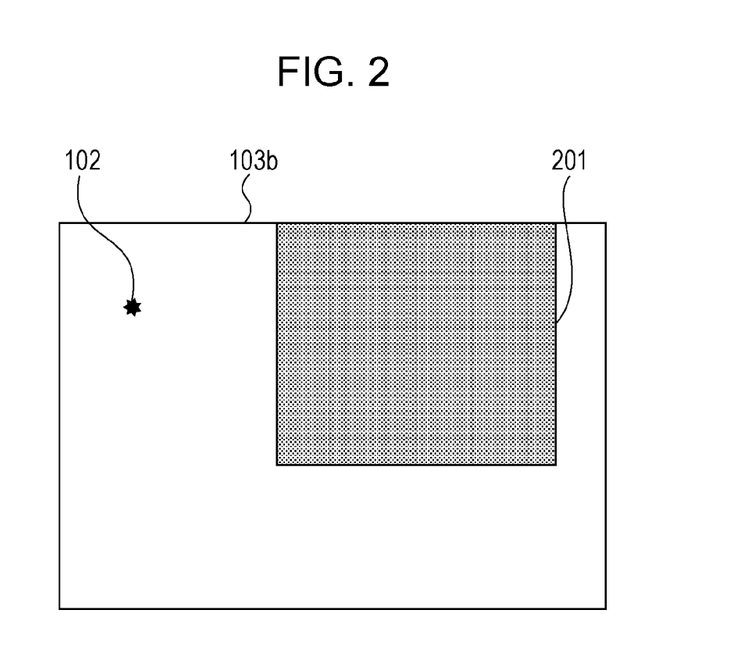
FIG. 2 illustrates an arrangement state of an optical absorber according to the first embodiment of the present invention.

To simplify the configuration of the apparatus, the optical absorber 102 may be desirably arranged in the plate 103a or 103b or on the surface of that plate. FIG. 2 illustrates an arrangement relationship between the optical absorber and a measurement region (actual measurement region 201) in which the analyte is arranged, when the plate 103b is viewed from the probe 104. Referring to FIG. 2, the optical absorber 102 with a certain size is arranged in a region other than the measurement region.

The size of the optical absorber 102 affects the frequencies of the photoacoustic wave generated from the optical absorber 102, and hence, is determined on the basis of a frequency band to be measured. In this embodiment, a fundamental frequency of a photoacoustic wave from a living body functions as a reference. The photoacoustic wave has a feature that a signal with a large N-type waveform appears. A peak frequency Fc of the N-type waveform can be expressed as follows:

$$Fc=0.66*c/D,$$

where D is a diameter if the optical absorber is spherical, and c is the sound speed in the analyte. If it is assumed that the spherical optical absorber has a diameter of 1 mm, Fc is obtained such that Fc=1 MHz. A tissue (malignant tumor) to be measured has a size in a range from about 1 to 20 mm. Thus, the optical absorber 102 has a size similar to the size of the tissue. The optical absorber 102 may be desirably spherical, because the intensity, frequency, and propagation of the photoacoustic wave generated from the optical absorber 102 can be predicted through analysis.

In this embodiment, the optical absorber 102 is included in the plate 103b. Alternatively, the optical absorber 102 may be provided on the surface of the plate 103b, in the plate 103a, or on the surface of the plate 103a. Still alternatively, the optical absorbers may be provided at both the plates 103a and 103b. Yet alternatively, if the plate 103a or 103b is not provided, the optical absorber may be provided on the surface of the probe. That is, the optical absorber 102 may be located at any position in the apparatus as long as the optical absorber 102 can be irradiated with the laser light and the photoacoustic wave arrives at the probe. The laser light source 100 that irradiates the optical absorber 102 with the light is also used as the laser light source 100 for normal diagnostic measurement in this embodiment. Alternatively, different laser light sources may be used for those purposes.

Further, the optical absorber 102 may include a plurality of optical absorbers 102. If only one optical absorber 102 is used, the probe is moved such that the optical absorber 102 is arranged above the center point of one of the elements included in the probe, and the intensity of the photoacoustic wave from the optical absorber 102 is measured. This operation is performed for every element of the probe. Accordingly, the intensity of the photoacoustic wave from the optical absorber 102 can be measured by all elements. The sensitivity of the probe according to this embodiment can be corrected. However, in this case, to obtain reception characteristic information of the plurality of receiving elements, the light irradiation has to be performed by the number of elements. This operation may take a time. If a plurality of optical absorbers 102 are prepared and the optical absorbers 102 are respectively arranged above the center points of the elements of the probe, the photoacoustic waves from the plurality of optical absorbers 102 can be measured simultaneously by all elements. In this case, the measurement for the sensitivity correction according to this embodiment is ended by the one-time measurement. If the plurality of optical absorbers 102 are used, the optical absorbers 102 desirably have the same size and are desirably made of the same material.

When the optical absorbers 102 are respectively arranged above the center points of the elements of the probe 104, at positions sufficiently close to the surface of the probe, the photoacoustic wave from the optical absorber arranged above the adjacent element is incident on the target element at a large angle. The element of the probe has a directivity for reception, and has a highest sensitivity to the acoustic wave being incident perpendicularly on the element. Regarding the directivity, when the optical absorber 102 is arranged above the center point of the element, the influence of the photoacoustic wave from the adjacent optical absorber is small.

In addition, in this embodiment, the plate 103b is present between the analyte and the probe 104. In this case, a time required for the photoacoustic wave to transmit through the plate 103b in the thickness direction may be a wasted time. That is, data from the time at which the laser light is emitted to the time at which the photoacoustic wave passes through the pressure plate 103 cannot be used for the reconfiguration of the diagnostic image. In other words, if the actual diagnostic measurement is carried out, the data for a predetermined period (or the time required for the photoacoustic wave to transmit through the pressure plate 103) from the time at which the laser light is emitted need not be acquired. That is, if the optical absorber 102 is present in the pressure plate 103, the photoacoustic wave from the optical absorber 102 does not adversely affect the measurement data during measurement. Accordingly, the optical absorber 102 is desirably provided at the plate 103b that is located close to the probe 104 rather than the plate 103a located close to the light source (laser light source 100).

[Calculation for Reception Characteristic]

Next, a procedure for calculating reception characteristic information of the plurality of receiving elements by performing the light irradiation while no analyte is present between the receiving elements and the plate 103b, will be described with reference to FIG. 1.

The photoacoustic wave generated from the optical absorber 102 as the result of the irradiation with the diffused pulsed light is received by all receiving elements of the probe 104. The optical absorber 102 is arranged at the certain position of the pressure plate. A probe drive unit 105 is used, so that the plurality of receiving elements of the probe 104 are successively moved to the position closest to the optical absorber 102, and hence the receiving elements can receive the photoacoustic wave. By using the probe drive unit 105 a plurality of times, all receiving elements of the probe 104 can receive the photoacoustic wave from the optical absorber 102, at the position closest to the optical absorber 102. Alternatively, the plurality of optical absorbers 102 may be prepared, and signals may be simultaneously received from the plurality of receiving elements as mentioned above.

Thus received signals of the receiving elements are transferred to a reception characteristic calculation unit 107. The reception characteristic calculation unit 107 calculates reception characteristic information of the plurality of receiving elements on the basis of the detected signals of the receiving elements. The "reception characteristic information" may be sensitivity characteristic information or frequency characteristic information of the receiving elements.

In this embodiment, a case, in which the reception characteristic calculation unit 107 calculates the sensitivity characteristic information as the reception characteristic information of the plurality of receiving elements, will be described. In this case, a maximum amplitude of the received signal is calculated. Since the pulsed light is emitted by an equivalent light quantity, each element receives the acoustic wave with an equivalent sound pressure, at the position closest to the optical absorber 102. If the maximum amplitudes of the received signals by the plurality of receiving elements are compared with one another, variation in sensitivity can be recognized.

Accordingly, variation in reception characteristic among the plurality of receiving elements can be recognized with a simple configuration unique to the photoacoustic apparatus.

[Correction of Detected Signal]

When the analyte is measured, if the variation in sensitivity occurs, the information about the inside of the analyte cannot be correctly acquired. Thus, to reduce the difference in sensitivity among the plurality of receiving elements, the detected signal when the probe 104 receives the acoustic wave generated in the analyte may be desirably corrected.

To correct the received signal, the signal processing unit 108 carries out an operation for canceling the calculated characteristic by using the sensitivity characteristic information calculated by the reception characteristic calculation unit 107. For example, if the sensitivity characteristic of each respective receiving element is calculated, the received signal is multiplied by the reciprocal of the calculated sensitivity.

Figure 3:
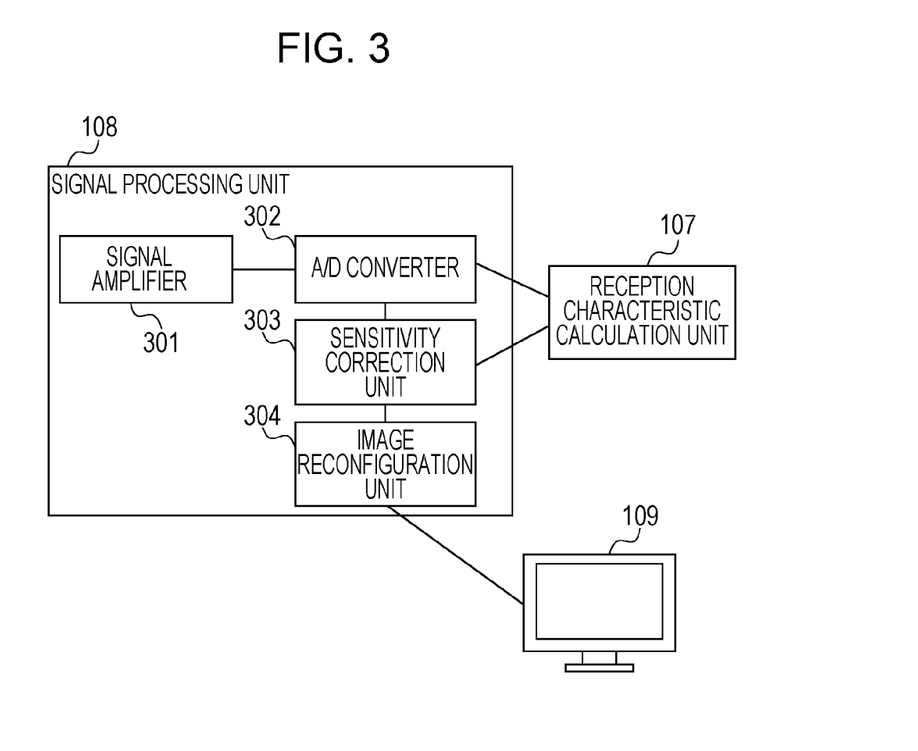
FIG. 3 is a block diagram showing the inside of a signal processing unit according to the first embodiment of the present invention.
Figure 4:
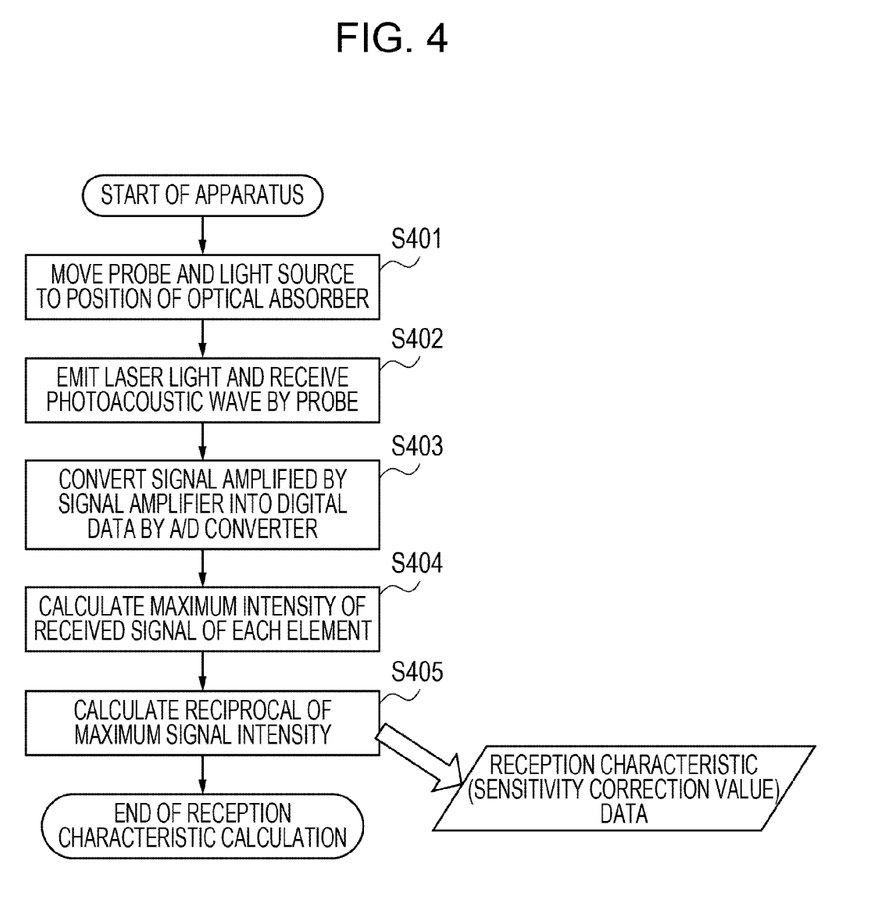
FIG. 4 is a flowchart showing an operational flow for calculating a reception characteristic according to the first embodiment of the present invention.

FIG. 3 illustrates inner blocks of the signal processing unit 108 according to this embodiment. The signal processing unit 108 includes a received signal amplifier 301, an A/D converter 302, a sensitivity correction unit 303, and an image reconfiguration unit 304. FIG. 4 illustrates an operational flow for calculating a reception characteristic according to this embodiment. The operational flow is part of the flow that acquires data for correcting the reception sensitivity. Hence, the operational flow is generally executed when the apparatus is started and before the actual measurement is performed. Of course, the operational flow may be performed during the measurement. In step S401 of the operational flow, the probe 104 and the laser light source 100 are moved to the position of the optical absorber 102. Then, in step S402, the laser light is emitted to cause the photoacoustic wave to be generated from the optical absorber 102. The probe 104 receives the photoacoustic wave and converts the received wave into the electric signal. In step S403, the A/D converter 302 converts the electric signal amplified by the signal amplifier 301 into digital data. The converted digital data is transmitted to the reception characteristic calculation unit 107. In step S404, the maximum intensity of the received signal of each element is calculated. In step S405, the reciprocal to the maximum signal intensity of each element is calculated, and the reception characteristic calculation unit 107 stores the calculation result as reception characteristic data (sensitivity correction value in this embodiment). In the operational flow, it is assumed that the plurality of optical absorbers 102 are provided and are respectively arranged above the center points of the receiving elements. Accordingly, the sensitivity correction data can be calculated by the one-time laser irradiation.

Figure 5:
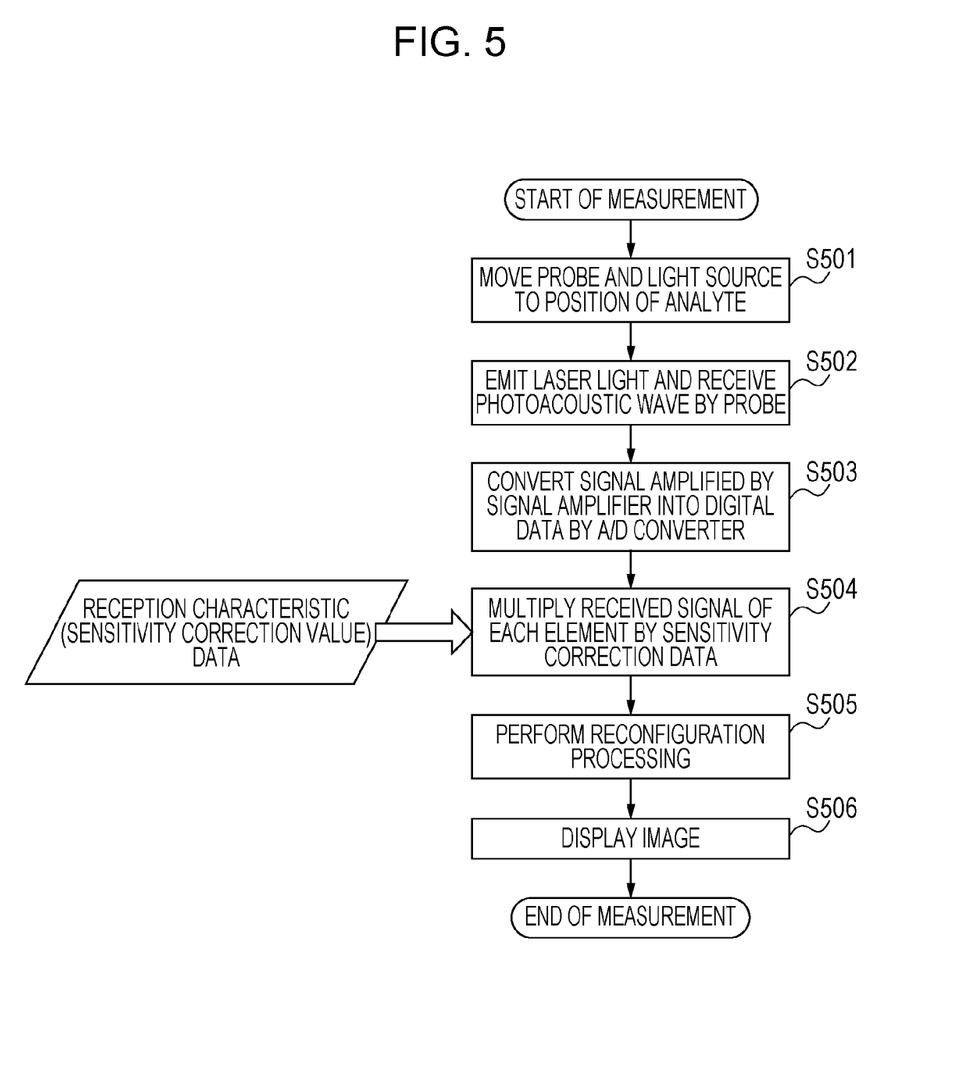
FIG. 5 is a flowchart showing an operational flow for correcting an actual measurement signal according to the first embodiment of the present invention.

In this embodiment, FIG. 5 illustrates an operational flow for correcting the actual measurement signal by using the measured reception characteristic data (sensitivity correction data). In step S501, the probe 104 and the laser light source 100 are moved to the position of the analyte to be measured. Then, in step S502, the laser light is emitted to cause the photoacoustic wave to be generated from the analyte. The probe 104 receives the photoacoustic wave and converts the received wave into the electric signal. In step S503, the A/D converter 302 converts the electric signal amplified by the signal amplifier 301 into digital data. For the converted digital data, the sensitivity correction unit 303 corrects the detected signal of each element by using the sensitivity correction data transmitted from the reception characteristic calculation unit 107. More specifically, in step S504, the signal intensity of each element is multiplied by the sensitivity correction value (or the reciprocal of the maximum signal intensity for each element of the received signal from the optical absorber 102) for each element. When the sensitivity correction data is multiplied by the received signal data in step S504, the sensitivity of each element is actually corrected. Accordingly, the difference in sensitivity among the receiving elements is corrected, and the variation in received signal data among the elements can be reduced. The received signal data after the sensitivity correction is transmitted to the image reconfiguration unit 304, and an image is reconfigured in step S505. Then, in step S506, the image is displayed on the image display unit 109.

With this embodiment, the influence by the variation in sensitivity of the probe is reduced, and hence correct information can be acquired by the analyte measurement. Accordingly, if an image is formed for the analyte measurement, an image with high accuracy can be obtained, and diagnosis with high accuracy can be made.

[Second Embodiment]

In a second embodiment, a case, in which the reception characteristic calculation unit 107 calculates the frequency characteristic information as the reception characteristic information of the plurality of receiving elements, will be described.

If the frequency characteristic is needed as the reception characteristic, frequency analysis such as fast Fourier transform (FFT) is performed. In the first embodiment, the variation in sensitivity among the elements is corrected by using the maximum signal intensity. In the second embodiment, the correction is performed on the basis of the frequency characteristic of each element. The reception characteristic calculation unit 107 does not merely calculate the maximum intensity of the received signal, but performs the frequency analysis by, for example, FFT. Accordingly, the signal intensity (power spectrum) for every frequency of the received signal can be calculated. The reciprocal of the power spectrum is calculated, and thus, sensitivity correction data with regard to the frequency characteristic is obtained.

The frequency-dependent sensitivity correction data is used for the actual measurement as follows. In step S504 in FIG. 5 according to the first embodiment, only one sensitivity correction value is calculated for each element, and the signal data of each element is merely multiplied by that sensitivity correction value. In this embodiment, since the frequency-dependent sensitivity correction data is used, the frequency analysis is performed for the received data from the analyte, for example, by FFT. The received signal data after the frequency analysis is multiplied by the frequency-dependent sensitivity correction data for each frequency. The received signal data after the frequency-dependent sensitivity correction is converted back into received signal data on the time axis; for example, by inverse fast Fourier transform (inverse FFT). With this flow, the frequency-dependent sensitivity correction can be performed.

In the first and second embodiments, as described above, since the photoacoustic waves from the actual measurement range that is larger than the aperture size of the probe 104 and from the optical absorber 102 arranged at a certain position are measured, the probe 104 includes a drive unit so that the probe 104 is moved to a desirable measurement position to face an irradiation portion of the laser diffused-light source, in synchronization with the laser diffused-light source. Particularly in this embodiment, the probe drive unit 105 serves as the drive unit for the probe, and a light source drive unit 106 for driving the laser light source and the light diffusing unit serves as the drive unit. The drive unit for the light source does not have to move the laser light source 100 and the optical system (light diffusing unit) 101, and may only move an optical system part, such as a mirror for reflecting laser light or a tool for adjusting an optical path, arranged so that the analyte or the optical absorber 102 is finally irradiated with the diffused light.

[Third Embodiment]

Figure 6:
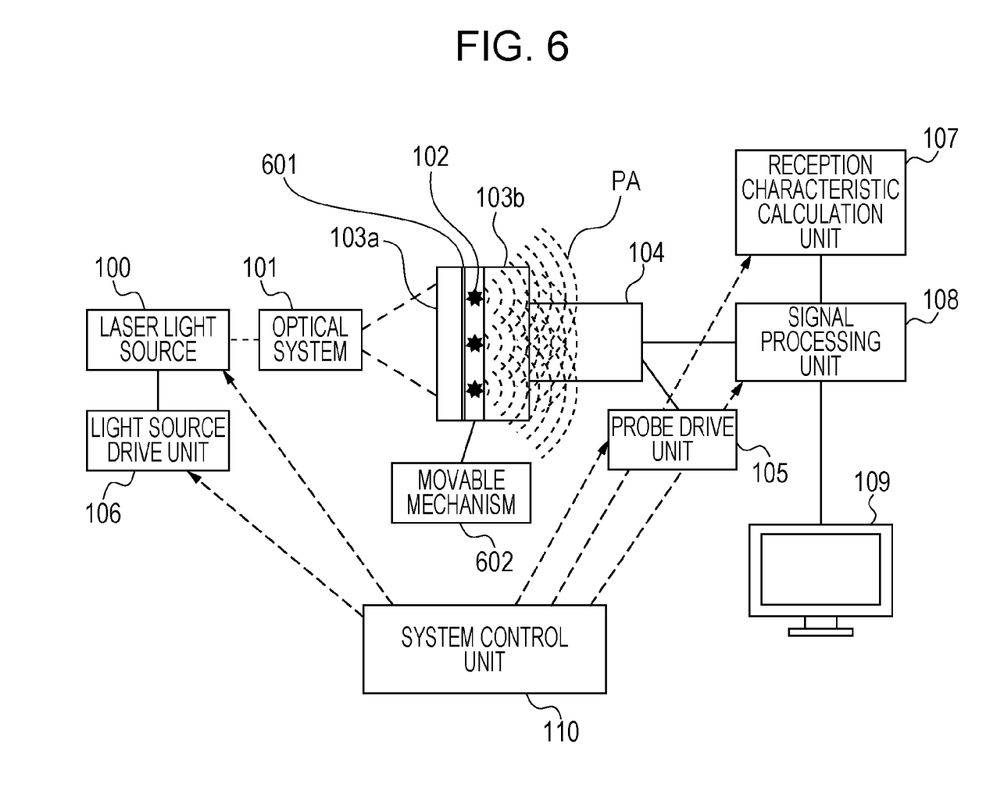
FIG. 6 is a block diagram schematically showing a configuration of a photoacoustic apparatus according to a third embodiment of the present invention.

FIG. 6 is a block diagram showing a photoacoustic apparatus according to a third embodiment of the present invention.

The photoacoustic apparatus according to this embodiment includes a characteristic measurement plate 601 having a plurality of optical absorbers 102, and a movable mechanism 602 that moves the characteristic measurement plate 601 so that the optical absorbers 102 are irradiated with pulsed laser light only during measurement for reception characteristics.

In this embodiment, the plurality of optical absorbers 102 are provided to allow reception characteristics of the plurality of receiving elements of the probe 104 to be measured. In this case, as the number of optical absorbers 102 becomes larger, the measurement time for the reception characteristics of the receiving elements of the probe 104 becomes shorter. However, in the case in which the plurality of optical absorbers 102 are present, if the optical absorbers 102 are arranged in a region other than the measurement region like the first embodiment, the mount area for such optical absorbers 102 has to be excessively large, resulting in an increase in size of the apparatus. To avoid this, the optical absorbers 102 are provided at the pressure plate 103 in the measurement region. In this case, the photoacoustic waves from the optical absorbers 102 are generated even during the normal diagnostic measurement. As described in the first embodiment, the photoacoustic wave from the position being sufficiently close to the probe 104 is ignorable during the actual diagnostic measurement. Also, since the photoacoustic wave coming from a position far from the receiving element of the probe 104 has a large incident angle due to the directivity of the probe 104, the photoacoustic wave less affects the measurement. However, if the number of optical absorbers 102 increases, the acoustic waves are generated by a large amount, and the effect of the acoustic waves become no longer ignorable.

Thus, provided in this embodiment is the characteristic measurement plate 601 having the plurality of optical absorbers 102 for reception characteristic measurement of the probe 104. In addition, the movable mechanism 602 is provided to move the characteristic measurement plate 308. When the reception characteristic of the probe 104 is measured, the characteristic measurement plate 601 is moved to the front of the probe 104, and the reception characteristic is measured. Then, the characteristic measurement plate 601 is moved away from the measurement region to a position at which the characteristic measurement plate 601 is not irradiated with the laser light to prevent the unused acoustic wave from being generated. In general, the measurement for the reception characteristic by using the characteristic measurement plate 601 is performed immediately after the apparatus is started. The reception characteristic of the probe 104 is measured, and then, the measurement result is used for correcting the reception characteristic for diagnosis.

[Fourth Embodiment]

Also, the present invention may be implemented by executing the following processing. In particular, the processing includes that a system or an apparatus is supplied with software (program) that provides the functions of any of the embodiments through a network or a recording medium of any kind, and a computer (or CPU, MPU, etc.) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.
[Reference Signs List]

The invention claimed is:

1. A method for controlling a photoacoustic apparatus comprising the steps of:
    providing a holding member;
    providing a light source outside of the holding member;
    providing a detecting unit including a plurality of receiving elements outside of the holding member;
    providing a plurality of optical absorbers in the holding member, each being located corresponding to each of the plurality of receiving elements;
    holding an analyte with the holding member configured to form an analyte region at which the analyte is held and a no-analyte region located in a remaining region other than the analyte region;
    irradiating the optical absorber with light in or on the no-analyte region through the holding member without passing through the analyte;
    receiving an acoustic wave generated from the optical absorbers in or on the non-analyte region with the detecting unit when the optical absorbers are irradiated thereto; and
    calculating reception characteristic information of the plurality of receiving elements on the basis of detected signals of the plurality of receiving elements.

2. The method according to claim 1, further comprising calculating reception sensitivity information of the plurality of receiving element.

3. The method according to claim 2, further comprising a step of correcting a reception signal received by the plurality of receiving elements based on the reception sensitivity information of the plurality of receiving elements calculated in the step of calculating.

4. The method according to claim 3, wherein the reception signal is multiplied by a reciprocal of the calculated reception sensitivity information in the step of correcting a reception signal received by the plurality of receiving elements.

5. The method according to claim 1, further comprising calculating a frequency characteristic information of the plurality of receiving elements.

6. The method according to claim 5, further comprising a step of correcting the reception signal received by the plurality of receiving elements based on the frequency characteristic information of the plurality of receiving elements calculated in the step of calculating.

7. The method according to claim 1, further comprising irradiating the optical absorber with light that has propagated through an uncompressed region of the holding member corresponding to a rest of a compressed region of the holding member.

8. The method according to claim 1, further comprising arranging each of the plurality of optical absorbers located at a center of the corresponding one of the receiving elements.

9. A photoacoustic apparatus comprising:
    a holding member configured to hold an analyte;
    a light source configured to irradiate light to the analyte transmitting through the holding member and located in opposition to the analyte with respect to the holding member;
    a detecting unit configured to detect acoustic wave through the holding member and located in opposition to the analyte with respect to the holding member;
    a plurality of optical absorbers disposed in or on the holding member;
    a signal processing unit configured to acquire information of the analyte from a detected signal of the acoustic wave from the detecting unit; and
    a reception characteristic calculation unit configured to calculate reception information based on the detected signal,
    wherein the holding member has a larger area than the analyte in a holding state and the holding member includes a holding region and an unholding region outside of the unholding region, and
    wherein the plurality of optical absorbers are located in the unholding region and are not located in the holding region.

* * * * *